United States Patent [19]

Burgoyne, Jr. William F. et al.

[11] Patent Number: 4,935,053
[45] Date of Patent: Jun. 19, 1990

[54] UNSATURATED HALOACETANILIDES

[75] Inventors: Burgoyne, Jr. William F., Emmaus, Pa.; Dale D. Dixon, Venice, Fla.

[73] Assignee: Air Products and Chemicals, Inc., Allentown, Pa.

[21] Appl. No.: 365,281

[22] Filed: Jun. 12, 1989

[51] Int. Cl.$^5$ .................... A01N 37/22; C07C 233/11
[52] U.S. Cl. .................................. 71/118; 564/211; 564/213
[58] Field of Search ................... 564/211, 213; 71/118

[56] References Cited

U.S. PATENT DOCUMENTS

| | | | |
|---|---|---|---|
| 4,028,093 | 6/1977 | Teach | 71/118 |
| 4,200,451 | 4/1980 | Vogel et al. | 71/118 |
| 4,322,553 | 3/1982 | Chupp | 564/209 |
| 4,324,580 | 4/1982 | Vogel et al. | 71/118 |

Primary Examiner—Glennon H. Hollrah
Assistant Examiner—P. O'Sullivan
Attorney, Agent, or Firm—Mark L. Rodgers; William F. Marsh; James C. Simmons

[57] ABSTRACT

Compounds having utility as herbicides for the pre-mergement treatment and control of grasses and weeds in crops such as rice and having the general structural formula:

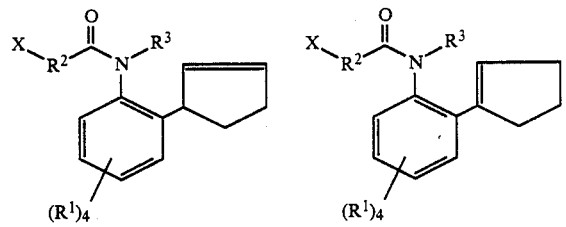

wherein each $R^1$ is independently H or a straight chain or branched $C_{1-10}$ alkyl or alkoxy group; $R^2$ is a straight chain or branched $C_{1-10}$ alkylene group; $R^3$ is —$CH_2(CH_2)_mO(CH_2)_nCH_3$ or

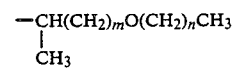

where both m and n are integers from 1 to 4; and X is a halogen.

12 Claims, No Drawings

UNSATURATED HALOACETANILIDES

TECHNICAL FIELD

The present invention relates to haloacetanilide compounds which demonstrate utility as herbicidal compositions for controlling weeds and grasses in agricultural crops.

BACKGROUND OF THE INVENTION

Herbicides and fungicides plays a significant role in ensuring that an adequate food supply at reasonable prices reaches the ever-increasing world population. The cultivation of rice is critical to the food supply of many countries. Itinerant weeds and grasses in the presence of rice, also a grass. dramatically reduce crop yield. Consequently. considerable research is being conducted to control, if not eliminate. such undesirable weeds and grasses. Herbicides and fungicides useful in the cultivation of rice must have selective biological activity wherein the unwanted grasses and weeds are caused to wither and die while the development of the rice is unaffected by the treatment.

Certain chloroacetanilides have been identified as herbicides for the pre-emergent treatment and control of weeds and grasses in rice crops. Representative chloroacetanilides are disclosed in U.S. Pat. No. 4.322,553 which relates to a process for preparing N-(halomethyl)acylamides as represented by the formula:

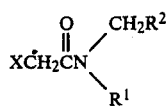

wherein X includes hydrogen. the halogens. a $C_1$–$C_6$ alkyl or haloalkyl radical, a radical a $C_3$–$C_7$ cycloalkyl radical, a phenyl or benzyl radical: R includes a $C_{1-20}$ alkyl radical and a phenyl radical. and $R^2$ is a chloro or bromo atom.

U.S. Pat. No. 4,324,580 teaches 2,6-diethyl-N-(1-methoxyprop-2'-yl)-[N]-chloroacetanilide as a plant growth regulating and herbicidal agent having improved stability in the soil.

U.S. Pat. No. 4,028,093 teaches meta-bis anilide derivatives which demonstrate utility as herbicides. The bis anilide derivatives are o represented by the formula:

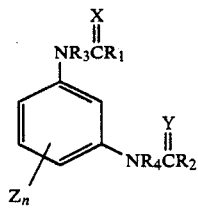

in which $R_1$ and $R_2$ are independently selected from hydrogen, alkyl, alkoxyalkyl, cycloalkyl, pinonyl, ethylcycloalkyl, lower alkenyl, halogenated lower alkyl, benzyl, ethylphenyl, 2,4-dichlorophenoxymethylene, styryl, furyl, phenyl or substituted phenyl in which the substituents are nitro, halogen, methyl or methoxy; $R_3$ and $R_4$ are independently selected from hydrogen, or lower alkyl; X and Y are independently selected from oxygen or sulfur; and Z is a halogen, nitro, amino, lower alkyl, lower alkoxy or trifluoromethyl and n is an integer having a value from 0 to 4. The compounds are stated to be effective herbicides for controlling grasses and broadleaf plants demonstrating both pre-emergent and post-emergent activity.

SUMMARY OF THE INVENTION

The present invention provides compounds having the general structural formulas:

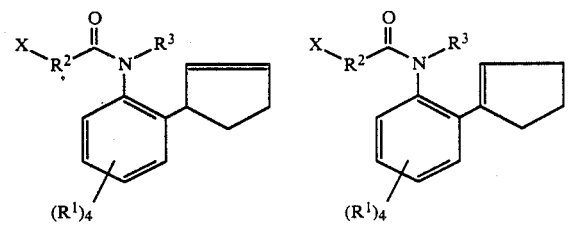

wherein each R is independently H or a straight chain or branched $C_{1-10}$ alkyl or alkoxy group; $R^2$ is a straight chain or branched $C_{1-10}$ alkylene group; $R^3$ is $-CH_2(CH_2)_mO(CH_2)_nCH_3$ or

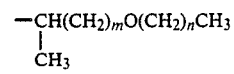

where both m and n are integers from 1 to 4; and X is a halogen.

The compounds are useful as herbicides in the premergement treatment and control of grasses and weeds in crops such as rice. They have the advantage over other herbicidal compositions in that they contain an additional reactive appendage; i e.. a cyclopentenyl moiety, ortho to the nitrogen. which allows for further modification of the compounds to tailor properties for a particular use.

DETAILED DESCRIPTION OF THE INVENTION

The present invention provides biologically active, unsaturated haloacetanilides which are useful in herbicidal applications. The unique feature of these compounds which distinguishes them from prior art compounds, such as those described in U.S. Pat. Nos. 4,258,196 and 4,200,451, is the presence of a cyclopentenyl moiety positioned ortho to the anilide nitrogen. This cyclopentenyl moiety serves as an additional reactive appendage which allows for further structure modification to enable the properties of the compound to be tailored for a specific application, or simply provides for a more active compound during use.

The compounds of the present invention can be represented by the general structural formulae:

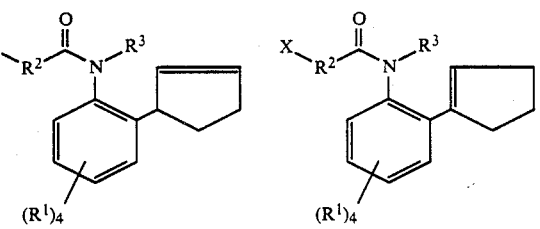

wherein each $R^1$ is independently H or a straight chain or branthed $C_{1-10}$ alkyl or alkoxy group; $R^2$ is a straight chain or branched $C_{1-10}$ alkylene group: $R^3$ is $-CH_2(CH_2)_mO(CH_2)_2CH_3$ or

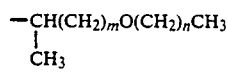

where both m and n are integers from 0 to 4; and X is a halogen, preferably chlorine. Preferred compounds of the present invention are those in which the $R^1$ group ortho to the nitrogen is either hydrogen, methyl, ethyl or isopropyl.

Unless otherwise indicated. the terms "alkyl," "alkylene" and "alkoxy" are used generically to include primary, secondary and tertiary groups. For such groups. these terms refer to those substituents having from 1 to 10 carbon atoms, inclusive, in both straight chain and branched chain configurations. Representative alkyl groups include methyl, ethyl, propyl, isopropyl, butyl, isobutyl, tert-butyl and the like. Representative alkylene groups include methylene. ethylene. propylene. butylene and the like. Representative alkoxy groups include methoxy, ethoxy, the isomeric configurations of butoxy and other alkoxy groups having from 5 to 10 carbon atoms.

The substituent designated as X is selected from the halogens including a fluorine atom (F), a chlorine atom (Cl), a bromine atom (Br) and an iodine atom (I), with a chlorine atom generally being preferred.

In a preferred synthesis technique. the compounds of the present invention are formed by first synthesizing cyclopentenyl aniline which is subsequently reacted with an appropriate compound, selected in accordance with the specific product desired. following the synthesis techniques set out below. Additionally, detailed synthesis of cyclopentenyl aniline is taught in E.P.O. Pat. Publication No. 277596 (10 Aug. 1988), assigned to Air Products and Chemicals, Inc.

The compounds of the present invention may be utilized as herbicides by o diluting the desired biologically active compound in a suitable solvent carrier such as water. Additives such as emulsifiers and surface-active agents may be added to enhance metabolic activity by influencing penetration. retention and surface tension. These herbicidal compositions may be applied by methods known in the art before the crop or weeds emerge from the ground (pre-emergence) or following emergence of the crop or weeds through the soil surface (post-emergence), although best results are obtained with pre-emergence use. An effective amount of the unsaturated haloacetanilide compound is utilized. i.e., that amount which provides the highest degree of herbicidal activity without harming the food crop. Such effective amounts are readily determined by those skilled in the art.

EXAMPLE 1

Preparation of Cyclonentenyl Aniline

A down-flow, fixed-bed microreactor was charged with 12 cc (6.00 g) of an amorphous acid catalyst comprised of 13% alumina and 87% silica. Aniline (1.5 cc/hr., 16.5 mmol/hr.), 1.02 cc/hr. (8.2 mmol/hr.) of dicyclopentadiene, and 5.69 cc/hr. (49.4 mmol/hr.) of pentane were then pumped over the catalyst bed at a pressure of 800 psig. The temperature of the catalyst bed was raised to 160° C. After a 24-hr. period. a sample of the reactor o effluent was taken and analyzed on a hydrocarbon-free basis by gas chromatography. Analyses of the reaction product obtained at 160° C. along with reaction products obtained at reaction temperatures of 180 and 200° C. are presented in Table 1.

TABLE 1

| | | Products Derived from Cyclopentadiene Addition to Aniline | | |
|---|---|---|---|---|
| Run No. | Temp. (°C.) | $PhNH_2$ | $2\text{-}(C_5H_6)PhNH_2^a$ | $4\text{-}(C_5H_6)PhNH_2^b$ |
| 1 | 160 | 75.26 | 22.13 | 2.61 |
| 2 | 180 | 34.05 | 57.07 | 8.88 |
| 3 | 200 | 38.37 | 41.17 | 20.46 |

[a] 2-(cyclopent-2-enyl)aniline
[b] 4-(cyclopent-2-enyl)aniline

EXAMPLE 2

Preparation of N-[2-(Cyclopent-2-enyl)phenyl]-N-(2-ethoxyethyl)-2-chloroacetamide

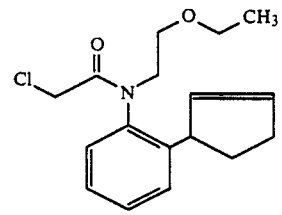

A solution of 30.00 g (188.4 mmol) of 2-(cyclopent-2-enyl)aniline from Example 1, 75.75 g (250 mmol) of triethylamine, and 81.43 g (750 mmol) of 2-chloroethyl ethyl ether was heated to 100° C., with magnetic stirring in a closed, 500 ml flask for 72 hr. The solution was cooled and diluted with 200 ml of ether, then the triethylamine hydrochloride precipitate was removed by vacuum filtration. Evaporation of the ether and residual 2-chloroethyl ethyl ether provided ca 40 g of a crude product consisting of, in part, 90.81 wt % of N-(2-ethyoxyethyl)-2-(cyclopent-2-enyl)aniline and 6.57 wt % of unreacted 2-(cyclopent-2-enyl)aniline. This crude product mixture was acylated directly.

The crude product described above was dissolved in 500 mL of ethyl acetate then added to a mixture of 50 g (0.595 mol) of sodium bicarbonate in 75 mL of water. With rapid stirring, 45.16 g (0.400 mol) of 2-chloroacetyl chloride was added proportionately over a period of 20 min. The mixture was then stirred an additional 4 hr. The layers were separated and the organic layer was dried over anhydrous magnesium sulfate. Evaporation of the solvent from the dried organic layer afforded ca 55 g of a product consisting of 89.3 wt % of N-[2-(cyclopent-2-enyl)phenyl]-N-(2-ethoxyethyl)-2-chloroacetamide and 7.72 wt % of N-[2-(cyclopent-2-enyl)phenyl]-2-chloroacetamide.

This product was purified by column chromatography (silica gel: Grade 60, 230–400 mesh; developed with 10:90 v/v ethyl acetate/methylene chloride) then by bulb-to-bulb distillation (bp. 165–175°/1.0 mm Hg). Satisfactory spectral and elemental analyses were obtained.

EXAMPLE 3

Preparation of N-[2-(cyclopent-2-enyl)phenyl]-N-(2-methoxyethyl)-2-chloroacetamide

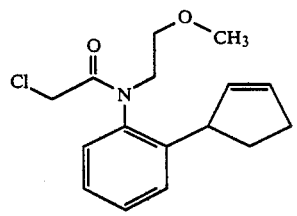

The preparation of N-[2-(cyclopent-2-enyl)phenyl]-N-(2-methoxyethyl)-2-chloroacetamide was conducted in a fashion analogous to example 2. Reaction of 30.00 g (188.4 mmol) of 2-(cyclopent-2-enyl)aniline, 75.75 g (750 mmol) of triethylamine, and 70.91 g (750 mmol) of 2-chloroethyl methyl ether at 100° C. in a closed, 500 mL flask for 56 hr. afforded ca. 40 g of a crude product consisting of, in part, 90.05 wt % of N-(2-methoxyethyl)-2-(cyclopent-2-enyl)aniline and 7.24 wt % of 2-(cyclopent-2-enyl)aniline. Acylation of this material with 2-chloroacetyl chloride provided ca. 50 g of a product consisting of, in part, 89.35 wt % of N-[2- cyclopent-2-enyl)phenyl]-N-(2-methoxyethyl)-2-chloroacetamide and 8.84 wt % of N-[2-(cyclopent-2-enyl)phenyl]-2-chloroacetamide. This material was purified by column chromatograph then bulb-to-bulb distillation (bp 165–175°C/1 mm/Hg).

EXAMPLE 4

(comparative)

Preparation of N-[2-(cyclopent-2-enyl)phenyl1-2-chloroacetamide

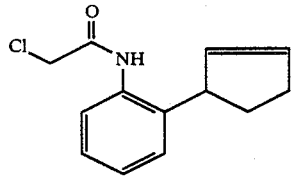

A solution of 10.00 g (62.8 mmol) of 2-(cyclopent-2-enyl)aniline from Example 1 in 150 mL of methylene chloride and 5.28 g (62.8 mmol) of sodium bicarbonate in 15 mL of water were combined with rapid stirring and cooled 0° C. with the aid of an ice bath. A solution of 7.099 (62.8 mmol) of chloroacetyl chloride in 25 mL of methylene chloride was then added dropwise through the course of 20 min. After an additional hour of vigorous stirring. the layers were separated and the organic layer was dried over anhydrous magnesium sulfate. Evaporation of the solvent in the organic layer and recrystallization of the precipitate with ether afforded 11.41 g (77% yield) of N-[2-(cyclopent-2-enyl)-phenyl]-2-chloroacetamide: mp 101°–102° C.

EXAMPLE 5

The compounds synthesized in Examples 2 and 3 above, as well as the comparative compound of Example 4, were tested for herbicidal activity using methods well known in the art. Additionally, for further comparison, several acetanilides which do not contain a cyclopentenyl group were also tested for herbicidal activity. The results of these tests are set out below:

| Compound | Herbicidal Activity |
|---|---|
| (prepared in Example 2) | Active |
| (prepared in Example 3) | Active |
| (prepared in Example 4) | Inactive |
| | Inactive |
| | Inactive |

The above results clearly demonstrated that the specific unsaturated haloacetanilides of the present invention are useful as herbicidal applications. whereas the other compounds tested did not exhibit herbicidal activity.

Having thus described the present invention, what is now deemed appropriate for Letters Pat. is set out in the following appended claims.

What is claimed is:

1. A compound having the general structural formula:

wherein each
- $R^1$ is independently H or a straight chain or branched $C_{1-10}$ alkyl or alkoxy group;
- $R^2$ a methylene group
- $R^3$ is $-CH_2(CH_2)_mO(CH_2)_nCH_3$ or $$-\underset{\underset{CH_3}{|}}{CH}(CH_2)_mO(CH_2)_nCH_3$$

where both m and n are integers from 0 to 4 and X is a halogen.

2. The compound of claim 1 wherein $R^2$ is $CH_2$.
3. The compound of claim 2 wherein X is Cl.
4. The compound of claim 3 wherein each $R^1$ is hydrogen.
5. The compound of claim 1 wherein $R^3$ is $-CH_2CH_2OCH_3$.
6. The compound of claim 1 wherein the $R^1$ which is ortho to the nitrogen is methyl.
7. The compound of claim 1 wherein the $R^1$ which is ortho to the nitrogen is ethyl.
8. The compound of claim 1 wherein $R^3$ is $-CH_2CH_2OCH_2CH_3$.
9. The compound of claim 1 wherein X is Cl, Br or I.
10. The compound of claim 1 which has the structural formula:

11. The compound of claim 1 which has the structural formula:

12. A herbicidal composition comprising an effective amount of a compound of claim 11 and an inert carrier.

* * * * *